United States Patent [19]

McCuaig

[11] Patent Number: 5,662,937
[45] Date of Patent: Sep. 2, 1997

[54] LONG LIFE DEODORANT COMPOSITION

[76] Inventor: Dorothy McCuaig, Box 238, Eastend, Saskatchewan, Sonoto, Canada

[21] Appl. No.: 516,062

[22] Filed: Aug. 17, 1995

[30] Foreign Application Priority Data

Aug. 26, 1994 [CA] Canada ................... 2310967

[51] Int. Cl.$^6$ ................ A61K 7/36; A61K 9/14; A61K 33/30
[52] U.S. Cl. ............ 424/489; 424/401; 424/65; 424/67; 514/951; 514/778
[58] Field of Search ................ 424/401, 65, 67, 424/489; 514/778, 951

[56] References Cited

U.S. PATENT DOCUMENTS

| | | | |
|---|---|---|---|
| 279,195 | 12/1883 | Slocomb et al. | 424/65 |
| 916,692 | 3/1909 | Foregger | 424/62 |
| 2,144,632 | 1/1939 | Melton | 167/92 |
| 3,632,350 | 1/1972 | Battista | 99/1 |
| 4,009,254 | 2/1977 | Renold | 424/59 |
| 4,421,128 | 12/1983 | Boulogne et al. | 132/88.5 |
| 4,454,118 | 6/1984 | Johnson | 424/95 |
| 4,478,853 | 10/1984 | Chaussee | 424/358 |
| 4,556,560 | 12/1985 | Buckingham | 424/145 |
| 4,868,220 | 9/1989 | Scheuffgen | 514/784 |
| 4,970,220 | 11/1990 | Chausee | 514/384 |
| 5,190,915 | 3/1993 | Behan et al. | 512/2 |
| 5,244,665 | 9/1993 | Natraj et al. | 424/401 |
| 5,306,486 | 4/1994 | McCook et al. | 424/59 |
| 5,310,556 | 5/1994 | Ziegler | 424/401 |

*Primary Examiner*—Thurman K. Page
*Assistant Examiner*—James M. Spear
*Attorney, Agent, or Firm*—Robert W. B. Bailey

[57] ABSTRACT

A long life deodorant composition lasting up to about 7 days for foot odor, and up to about 15 days underarm, includes specially treated cornstarch or oat starch as a substitute for talc. Additionally the treated starch acts as a spreading agent, giving a silky smooth effect. Citric acid, an increased proportion of zinc oxide and aloe vera concentrate are advantageously included in the deodorant.

20 Claims, No Drawings

LONG LIFE DEODORANT COMPOSITION

This invention relates to long life deodorant compositions, deodorant compositions are well known, long life ones less so.

The present invention contemplates using treated starches in long life deodorants, as a substitute for talc, specially treated cornstarch and oat starch have been rigorously tested. It further contemplates using citric acid to improve deodorant life.

Although the invention will be described and referred to specifically as it relates to such treated starches and citric acid in long life deodorant compositions, it will be understood that the principles of this invention are equally applicable to similar spreading agents of similar properties and similar deodorant compositions and accordingly, it will be understood that the invention is not limited to such treated starches and deodorant compositions.

BACKGROUND OF INVENTION

The components of the deodorant composition petroleum jelly, zinc oxide, regular cornstarch, arnica oil, calendula oil, vitamin E, citric acid are all known to be used in skin contact preparations.

PRIOR ART

U.S. Pat. No. 279,195, Jun. 12, 1883, Slocomb et al., teaches a three part composition of ⅔ bicarbonate of soda, ⅙ cornstarch, ⅙ rice flour.

U.S. Pat. No. 916,692, Mar. 30, 1909, Foregger, teaches a deodorant composition containing calcium, magnesium, strontium and zinc perborate and peroxide, and sodium perborate. The rest of the composition is a standard skin preparation, exemplified are talc and petroleum jelly.

U.S. Pat. No. 2,144,632, Jan. 24, 1939, Melton, teaches a deodorant composition containing a peroxide, zinc peroxide is exemplified, an absorbent material, kaolin exemplified, and a neutral material, talc or precipitated chalk exemplified, zinc oxide is present.

U.S. Pat. No. 3,632,350, Jan. 4, 1972, Battista teaches petroleum jelly, zinc oxide, cornstarch, and citric acid in a food composition.

U.S. Pat. Nos. 4,009,254, Feb. 22, 1977, Renold, 4,478,853, Oct. 23, 1984, Chaussee, 4,556,560, Dec. 3, 1985, Buckingham, 4,970,220, Nov. 13, 1990, Chaussee, all teach deodorant compositions containing petroleum jelly and zinc oxide.

U.S. Pat. No. 5,190,915, Mar. 2, 1993, Behan, teaches, deodorant compositions containing petroleum jelly and citric acid.

U.S. Pat. No. 4,868,220, Sep. 19, 1989, Scheuffgen, teaches a composition including petroleum jelly, zinc oxide, and calendula oil.

U.S. Pat. Nos. 4,454,118, Jun. 12, 1984, Johnson, 5,306,486, Apr. 26, McCook, 5,310,556, May 10, 1994, Ziegler, all teach cosmetic/skin compositions including petroleum jelly, zinc oxide and vitamin E.

U.S. Pat. No. 5,244,665, Sep. 14, 1993, Natraj, teaches a cosmetic composition including petroleum jelly, zinc oxide, citric acid and vitamin E.

Lavilin, manufactured in Israel by Hlavin Cosmetics includes petroleum jelly, potato starch, talc, zinc oxide, calendula oil, arnica oil, vitamin E, ascorbyl palmitate, citric acid and scent concentrate.

Canamino Inc., has developed a number of products primarily based on finely milled fractionated oatmeal, one of these is a surface treated pure oat starch, which can be used instead of talc in skin contact products. A similar surface treated cornstarch can be also be used instead of talc. Straight substitution does not produce the identical result, each application must be custom tailored.

It is a principal object of the invention to provide a long life deodorant. It is another principal object of the invention as far as possible to provide a vegetable based deodorant. It is a subsidiary object of the invention to provide a smooth, silky easily applicable deodorant. It is a further object of the invention to provide a deodorant effective up to about 7 days for foot odor, and up to about 15 days underarm. Other objects will be apparent to those skilled in the art from the following specification and appended claims.

DESCRIPTION OF THE INVENTION

The invention is directed in one form to an improved deodorant composition comprising zinc oxide. The improvement provides a spreads a starch spreading agent having an average particle size up to about 14 microns. Preferably the composition includes citric acid, and preferably vitamin E concentrate, more preferably at least about 13% of zinc oxide, most preferably aloe vera concentrate. When oat starch is used the particle size typically averages 8 microns, when cornstarch is used the particle size typically averages 14 microns. Preferably the starch is treated with an N-alkanoyl amino acid, more preferably lauroyl lysine.

In a second form the invention is directed to a deodorant composition of petroleum jelly, regular cornstarch, talc, zinc oxide, arnica oil, calendula oil, vitamin E concentrate, citric acid and scent concentrate.

In a third form the invention is directed to an improved deodorant composition comprising petroleum jelly, regular cornstarch, zinc oxide, arnica oil, calendula oil, vitamin E concentrate, citric acid and scent concentrate, the improvement comprising additional starch having an average particle size up to about 14 microns. When oat starch is used the particle size typically averages 8 microns, when cornstarch is used the particle size typically averages 14 microns. Preferably the starch is treated with an N-alkanoyl amino acid, more preferably lauroyl lysine. Preferably aloe vera concentrate is included. Preferably the composition includes petroleum jelly about 32 to 33½%, regular cornstarch about 22 to 23½% zinc oxide about 13 to 17%, arnica oil about 5.3 to 5.6%, calendula oil about 0.65 to 0.70%, vitamin E concentrate about 0.44 to 0.46%, citric acid about 0.32 to 0.36%, scent concentrate about 0.11 to 0.12%, and about 22 to 23½% selected from the group consisting of lauroyl lysine treated oat starch having a particle size averaging about 8 microns and lauroyl lysine treated corn starch having a particle size averaging about 14 microns.

The percentages given above are by weight, in some cases where volume measures are used the density has been assumed to be about 1. That is mls are equated to gms.

EXAMPLES

Throughout the examples vitamin E concentrate refers to Covi-ox T-70, a commercially available concentrate of at least 70% by weight of a mixture of $\alpha$-, $\beta$-, $\gamma$-, $\delta$- tocopherols.

PRIOR ART EXAMPLE

A deodorant composition consisted of

| | | |
|---|---|---|
| Petroleum jelly | 720 g | 33.4% |
| Regular cornstarch | 500 g | 23.2% |
| Talc | 500 g | 23.2% |
| Zinc oxide | 285 g | 13.2% |
| Arnica oil | 120 g | 5.57% |
| Calendula oil | 15 ml | 0.70% |
| Vitamin E concentrate | 10 ml | 0.46% |
| Scent concentrate | 2.5 ml | 0.12% | which had an effective life of 5 days for foot odor and 10 days underarm.

Example I

A deodorant composition was formed consisting of

| | | |
|---|---|---|
| Petroleum jelly | 720 g | 33.3% |
| Regular cornstarch | 500 g | 23.2% |
| Talc | 500 g | 23.2% |
| Zinc oxide | 285 g | 13.2% |
| Arnica oil | 120 g | 5.56% |
| Calendula oil | 15 ml | 0.70% |
| Vitamin E concentrate | 10 ml | 0.46% |
| Citric Acid | 7 g | 0.32% |
| Scent concentrate | 2.5 ml | 0.12% |

7 g citric acid was added, the composition was tested and found to be a very effective long life deodorant lasting up to 7 days for foot odor, and up to 15 days underarm. However it proved difficult to apply, on account of its thickness and density.

Example II

A deodorant composition was formed consisting of

| | | |
|---|---|---|
| Petroleum jelly | 720 g | 33.3% |
| Regular cornstarch | 500 g | 23.2% |
| Treated cornstarch/oat starch | 500 g | 23.2% |
| Zinc oxide | 285 g | 13.2% |
| Arnica oil | 120 g | 5.56% |
| Calendula oil | 15 ml | 0.69% |
| Vitamin E concentrate | 10 ml | 0.46% |
| Citric Acid | 7 g | 0.32% |
| Scent concentrate | 2.5 ml | 0.12% |

The treated cornstarch is cornstarch JALB, is a lauroyl lysine surface treated cornstarch giving it a smooth, silky feel. The treated cornstarch has a particle size averaging about 14 microns (0.014 mm). The treated oat starch is Ostar™, is also lauroyl lysine surface treated oat starch, giving the same smooth silky feel. The treated oat starch has the normal particle size of about 8 microns (0.008 mm), and is thus somewhat finer than the treated cornstarch. Both treated starches are milled to remove protein, and are commercially available from Canamino Inc., Saskatoon, Saskatchewan. They were used to replace talc in the prior art example. Talc is a by-product of asbestos, and it was felt that a plant product was preferable to a mineral product. This composition was tested and found to be an effective deodorant lasting up to 2 or 3 days for foot odor, and 4 or 5 days underarm. The product was found to be silky smooth and very much easier to apply.

As would be understood by those skilled in the art starches having the same spreading properties and silky smooth feel effect could be substituted for these treated starches.

Example III

A deodorant composition was formed consisting of

| | | |
|---|---|---|
| Petroleum jelly | 720 g | 33.0% |
| Regular cornstarch | 500 g | 22.9% |
| Treated cornstarch/oat starch | 500 g | 22.9% |
| Zinc oxide | 305 g | 14.0% |
| Arnica oil | 120 g | 5.51% |
| Calendula oil | 15 ml | 0.69% |
| Vitamin E concentrate | 10 ml | 0.46% |
| Citric Acid | 7 g | 0.32% |
| Scent concentrate | 2.5 ml | 0.11% |

The proportion of zinc oxide was increased by 20 g, lengthening the deodorant's effective life to 3 or 4 days for foot odor, and 5 or 6 days underarm.

Example IV

A deodorant composition was formed consisting of

| | | |
|---|---|---|
| Petroleum jelly | 720 g | 32.7% |
| Regular cornstarch | 500 g | 22.7% |
| Treated cornstarch/oat starch | 500 g | 22.7% |
| Zinc oxide | 325 g | 14.8% |
| Arnica oil | 120 g | 5.45% |
| Calendula oil | 15 ml | 0.68% |
| Vitamin E concentrate | 10 ml | 0.45% |
| Citric Acid | 7.5 g | 0.34% |
| Scent concentrate | 2.5 ml | 0.11% |

The proportion of zinc oxide was increased by 40 g, and citric acid by 0.5 g, lengthening the deodorant's effective life to 4 or 5 days for foot odor, and 6 or 7 days underarm.

Example V

A deodorant composition was formed consisting of

| | | |
|---|---|---|
| Petroleum jelly | 720 g | 32.1% |
| Regular cornstarch | 500 g | 22.3% |
| Treated cornstarch/oat starch | 500 g | 22.3% |
| Zinc oxide | 370 g | 16.5% |
| Arnica oil | 120 g | 5.34% |
| Calendula oil | 15 ml | 0.67% |
| Vitamin E concentrate | 10 ml | 0.45% |
| Citric Acid | 8 g | 0.36% |
| Scent concentrate | 2.5 ml | 0.11% |

The proportion of zinc oxide was increased by 85 g, and citric acid by 1 g, lengthening the deodorant's effective life to up to 7 days for foot odor, and up to 14 days underarm.

Example VI

A deodorant composition was formed consisting of

| | | |
|---|---|---|
| Petroleum jelly | 720 g | 31.9% |
| Regular cornstarch | 500 g | 22.2% |
| Treated cornstarch/oat starch | 500 g | 22.2% |
| Zinc oxide | 370 g | 16.4% |
| Arnica oil | 120 g | 5.32% |
| Calendula oil | 15 ml | 0.67% |
| Vitamin E concentrate | 10 ml | 0.44% |
| Aloe Vera concentrate | 10 ml | 0.44% |
| Citric Acid | 8 g | 0.35% |
| Scent concentrate | 2.5 ml | 0.11% |

The proportion of zinc oxide was increased by 85 g, and citric acid by 1 g, and 10 ml of Aloe Vera concentrate was added, lengthening the deodorant's effective life to up to 8 days for foot odor, and up to 15 days underarm.

As those skilled in the art would realize these preferred described details and materials and components can be subjected to substantial variation, modification, change, alteration, and substitution without affecting or modifying the function of the described embodiments. Although embodiments of the invention have been described above, it is not limited thereto, and it will be apparent to persons skilled in the art that numerous modifications and variations form part of the present invention insofar as they do not depart from the spirit, nature and scope of the claimed and described invention.

I claim:

1. In a deodorant composition comprising zinc oxide and citric acid, the improvement comprising a starch spreading agent having an average particle size up to about 14 microns.

2. A composition of claim 1, comprising at least about 13% of zinc oxide.

3. A composition of claim 2, additionally comprising aloe vera concentrate.

4. A composition of claim 1 comprising lauroyl lysine treated oat starch having a particle size averaging about 8 microns.

5. A composition of claim 4, additionally comprising aloe vera concentrate.

6. A composition of claim 1, comprising lauroyl lysine treated corn starch having a particle size averaging about 14 microns.

7. A composition of claim 6, additionally comprising aloe vera concentrate.

8. A composition of claim 1, additionally comprising vitamin E concentrate.

9. A deodorant composition comprising petroleum jelly, regular cornstarch, talc, zinc oxide, arnica oil calendula oil, vitamin E concentrate, citric acid and scent concentrate.

10. A composition of claim 9 comprising petroleum jelly about 33.3%, regular cornstarch about 23.2%, talc about 23.2%, zinc oxide about 13.2%, arnica oil about 5.56%, calendula oil about 0.70%, vitamin E concentrate about 0.46%, citric acid about 0.32%, scent concentrate about 0.12%.

11. In a deodorant composition comprising petroleum jelly, regular cornstarch, zinc oxide, arnica oil, calendula oil, vitamin E concentrate, citric acid and scent concentrate, the improvement comprising additional starch having an average particle size up to about 14 microns.

12. A composition of claim 11 wherein said additional starch is lauroyl lysine treated oat starch having a particle size averaging about 8 microns.

13. A composition of claim 11 wherein said additional starch is lauroyl lysine treated corn starch having a particle size averaging about 14 microns.

14. A composition of claim 11, wherein said composition additionally includes aloe vera concentrate.

15. A composition of claim 11 comprising petroleum jelly about 32 to 33½%, regular cornstarch about 22 to 23½%, zinc oxide about 13 to 17%, arnica oil about 5.3 to 5.6%, calendula oil about 0.65 to 0.70%, vitamin E concentrate about 0.44 to 0.46%, citric acid about 0.32 to 0.36%, scent concentrate about 0.11 to 0.12%, and about 22 to 23½% selected from the group consisting of lauroyl lysine treated oat starch having a particle size averaging about 8 microns and lauroyl lysine treated corn starch having a particle size averaging about 14 microns.

16. A composition of claim 11 comprising petroleum jelly about 33.3%, regular cornstarch about 23.2%, zinc oxide about 13.2%, arnica oil about 5.56%, calendula oil about 0.69%, vitamin E concentrate about 0.46%, citric acid about 0.32%, scent concentrate about 0.11%, and about 23.2% selected from the group consisting of lauroyl lysine treated oat starch having a particle size averaging about 8 microns and lauroyl lysine treated corn starch having a particle size averaging about 14 microns.

17. A composition of claim 11 comprising petroleum jelly about 33.0%, regular cornstarch about 22.9%, zinc oxide about 14.0%, arnica oil about 5.51%, calendula oil about 0.69%, vitamin E concentrate about 0.46%, citric acid about 0.32%, scent concentrate about 0.11%, and about 22.9% selected from the group consisting of lauroyl lysine treated oat starch having a particle size averaging about 8 microns and lauroyl lysine treated corn starch having a particle size averaging about 14 microns.

18. A composition of claim 11 comprising petroleum jelly about 32.7%, regular cornstarch about 22.7%, zinc oxide about 14.8%, arnica oil about 5.45%, calendula oil about 0.68%, vitamin E concentrate about 0.45%, citric acid about 0.34%, scent concentrate about 0.11%, and about 22.7% selected from the group consisting of lauroyl lysine treated oat starch having a particle size averaging about 8 microns and lauroyl lysine treated corn starch having a particle size averaging about 14 microns.

19. A composition of claim 11 comprising petroleum jelly about 32.1%, regular cornstarch about 22.3%, zinc oxide about 16.5%, arnica oil about 5.3%, calendula oil about 0.67%, vitamin E concentrate about 0.45%, citric acid about 0.36%, scent concentrate about 0.11%, and about 22.3% selected from the group consisting of lauroyl lysine treated oat starch having a particle size averaging about 8 microns and lauroyl lysine treated corn starch having a particle size averaging about 14 microns.

20. A composition of claim 14 comprising petroleum jelly about 31.9%, regular cornstarch about 22.2%, zinc oxide about 16.%, arnica oil about 5.32%, calendula oil about 0.67%, vitamin E concentrate about 0.44%, aloe vera concentrate about 0.4%, citric acid about 0.35%, scent concentrate about 0.11%, and about 22.24 selected from the group consisting of lauroyl lysine treated oat starch having a particle size averaging about 8 microns and lauroyl lysine treated corn starch having a particle size averaging about 14 microns.

* * * * *